United States Patent [19]
Bonaldo

[11] Patent Number: 5,807,347
[45] Date of Patent: Sep. 15, 1998

[54] MEDICAL VALVE ELEMENT

[76] Inventor: Jean M. Bonaldo, 1453 N. Tulare Way, Upland, Calif. 91780

[21] Appl. No.: 575,272

[22] Filed: Dec. 21, 1995

[51] Int. Cl.$^6$ ..................................................... A61M 5/00
[52] U.S. Cl. ............................................. 604/246; 604/86
[58] Field of Search ................................. 604/88, 86, 87, 604/201–202, 236–237, 244, 246, 284, 198, 162, 171; 251/149.1

[56] References Cited

U.S. PATENT DOCUMENTS

| | | | |
|---|---|---|---|
| 3,134,380 | 5/1964 | Armao | 128/215 |
| 4,457,749 | 7/1984 | Bellotti et al. | 604/29 |
| 4,512,766 | 4/1985 | Vaillancourt | 604/169 |
| 4,725,267 | 2/1988 | Vaillancourt | 604/192 |
| 4,915,697 | 4/1990 | DuPont | 604/192 |
| 5,015,242 | 5/1991 | Heifetz | 604/198 |
| 5,273,533 | 12/1993 | Bonaldo | 604/83 |
| 5,306,243 | 4/1994 | Bonaldo | 604/86 |
| 5,380,306 | 1/1995 | Brinon | 604/244 |
| 5,487,728 | 1/1996 | Vaillancourt | 604/86 |
| 5,607,392 | 3/1997 | Kanner | 604/86 |

*Primary Examiner*—John D. Yasko
*Attorney, Agent, or Firm*—Lockwood, Alex, FitzGibbon & Cummings

[57] ABSTRACT

A medical valve element has a first solid portion of circular cross-section, a second cylindrical portion with a frustoconical interior passage, and a third hollow cylindrical portion featuring peripheral grooves. The valve element is made of elastomeric material and the first portion is surrounded by a solid metallic collar. The valve element is used in a medical valve. The valve has a cannula mounded on a hub and fixed in a fluid conduit so that the cannula points upstream. The elastomeric valve element is mounted on the hub within the conduit so as to enclose the cannula. In use, the valve element is compressed by application of a medical appliance to the valve element first portion to cause the cannula point to pierce the first portion to provide a path for fluid flow through the conduit. The collar causes the valve first portion to reseal upon removal of the medical appliance and expansion of the valve element back to its original condition.

18 Claims, 3 Drawing Sheets

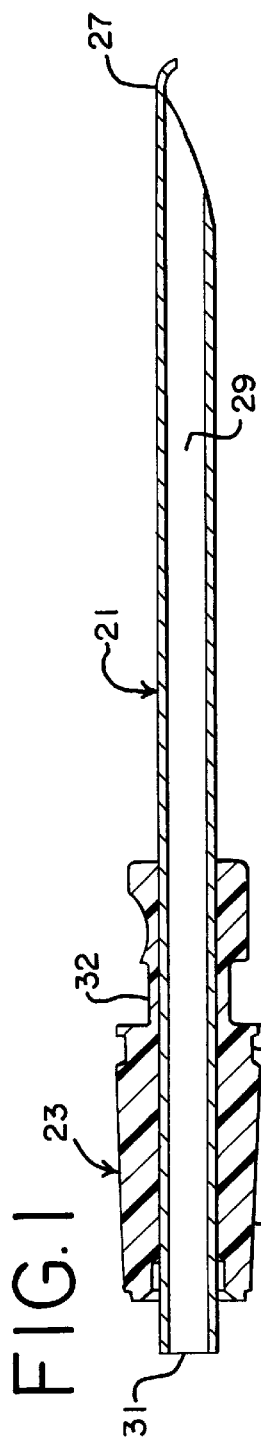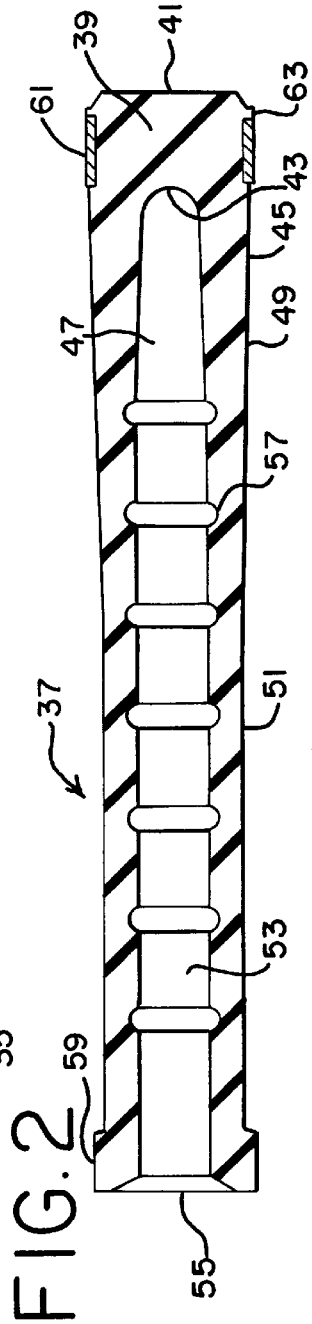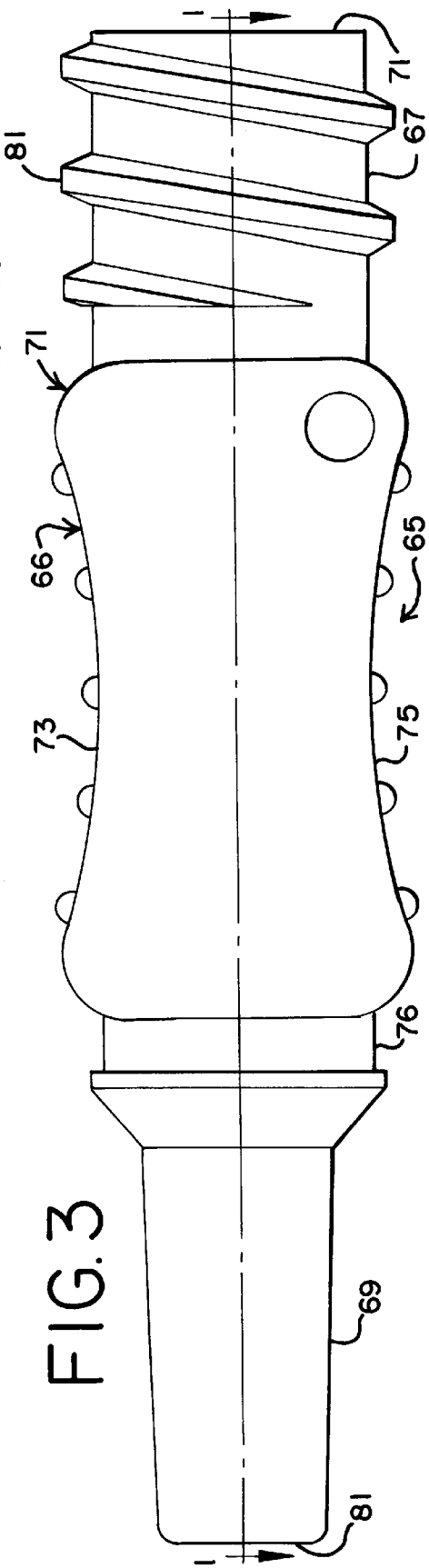

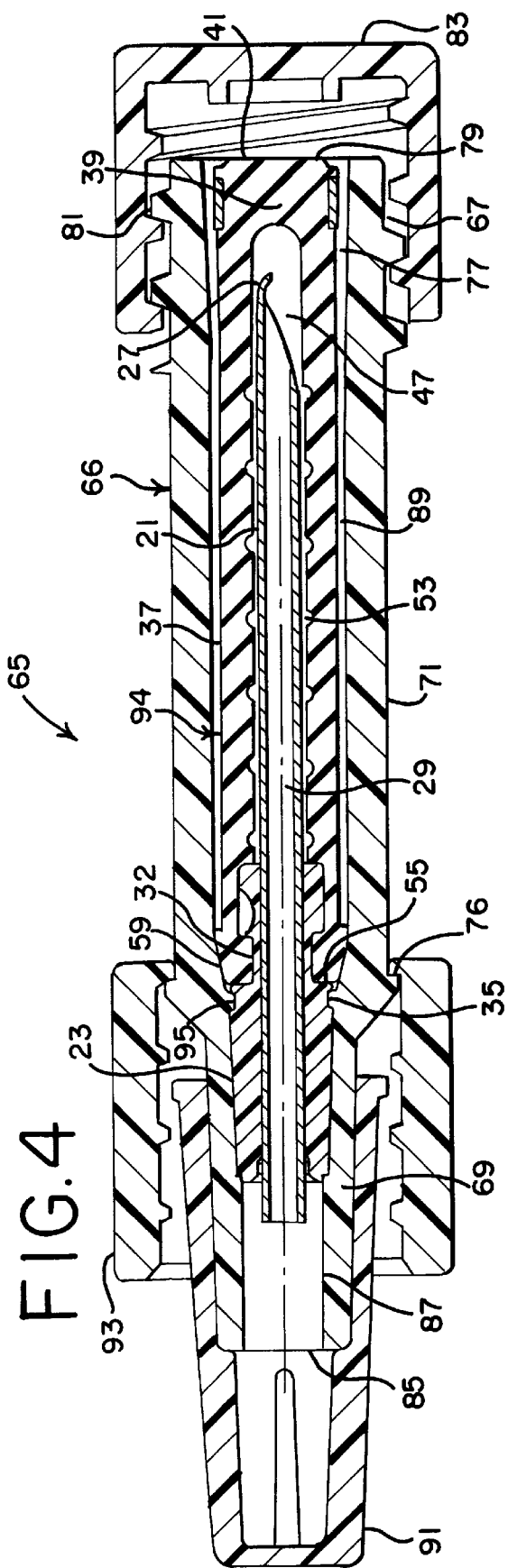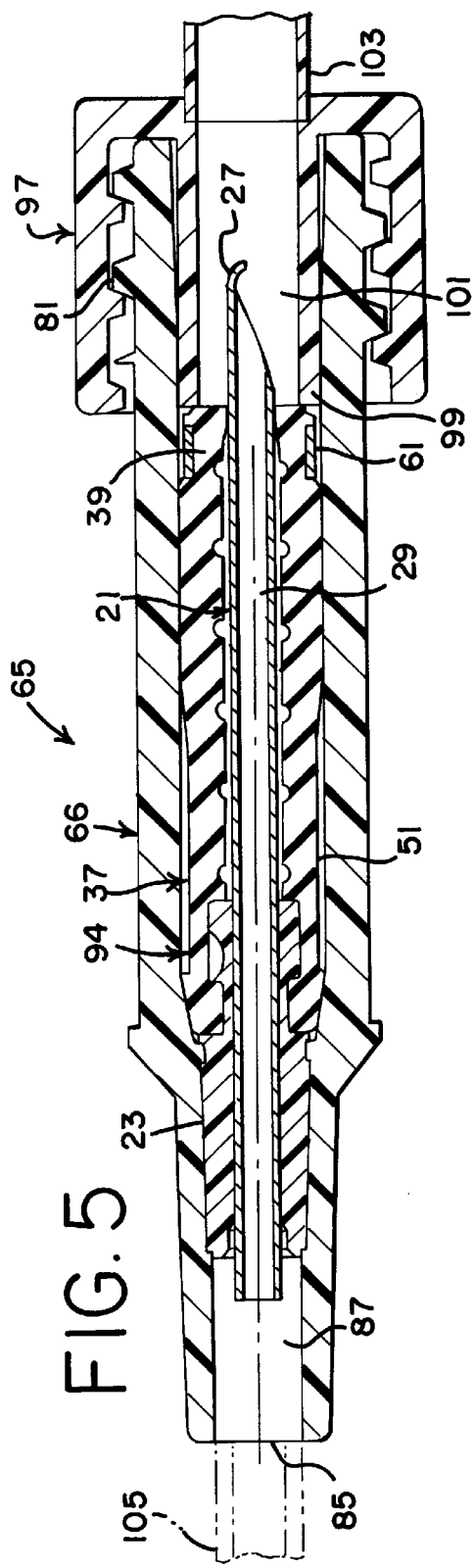

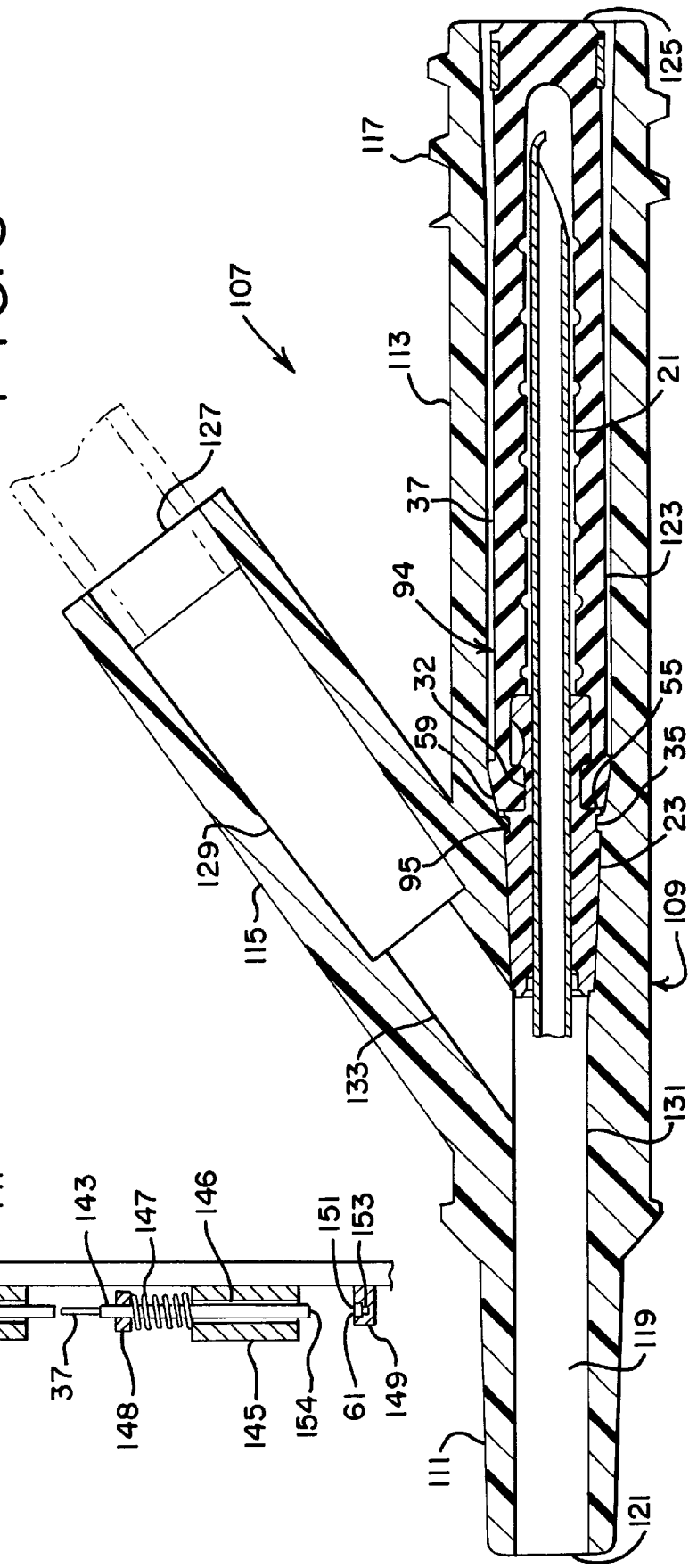

MEDICAL VALVE ELEMENT

BACKGROUND OF THE INVENTION

1. Field of the Invention

The present invention relates generally to a valve element for medical use to prevent the back-flow of blood or other fluid through the valve element and, more particularly, to an elongated flexible valve element that is penetrated by a cannula when in the open position and has a collar that effectuates resealing when it is in the closed position and a method for fitting the collar onto the valve element during its manufacture.

2. Description of the Prior Art and Discussion

U.S. Pat. No. 4,512,766, issued Apr. 23, 1995 to Vincent L. Vailancourt, discloses a valve mechanism for catheter use to avoid fluid backflow, including an elastomeric self-sealing valve element which may be pierced by an external needle used to insert a catheter.

U.S. Pat. Nos. 5,273,533 and 5,306,243, issued Dec. 28, 1993 and Apr. 26, 1994, respectively, to Jean M. Bonaldo, disclose a valve for medical use in a fluid conduit wherein a cannula is enclosed in an elastomeric valve element. In the open condition, the valve element is compressed by application of a medical fitting so that the cannula pierces the valve element to provide a path for fluid flow.

Many other medical valve designs also utilize elastomeric materials that are pierced by cannulas. While these devices have been found to work adequately, according to the present invention longevity and pressure handling capability may be improved by surrounding the flexible valve element, near the end that is penetrated, with a collar. By sizing the inner diameter of such a collar so that it exerts a radially compressive force, the penetrated portion of the valve element more readily and tightly seals upon removal of a piercing cannula.

It is, therefore, an object of the present invention to provide a flexible valve element featuring a surrounding collar.

Another object of the invention is the provision of a method of fitting the collar around the flexible valve element during its manufacture.

SUMMARY OF THE INVENTION

The present invention is directed to a medical valve element and its manufacture. The elongated flexible valve element has a first portion of solid circular cross-section and a second portion of circular cross-section adjacent to the first portion with a longitudinal central passage therethrough. A collar surrounds the first portion of the valve element so as to exert a radially comring. The valve element may be used as part of a medical valve in a fluid conduit. In such instances, a hub is fixed within the conduit so as to hold a hollow cannula with a pointed end so that the pointed end points toward the conduit inlet. The valve element is fixed within the conduit with respect to the hub so that the pointed end of the cannula is disposed within the central passage of the valve element.

A method of fitting the collar onto the elongated flexible valve element during its manufacture is also provided. The valve element is propelled in an axial direction with pressurized fluid. The propelled valve element is compressed radially and directed so that a portion of it is axially inserted through the collar while still in a compressed condition. This results in the collar being fitted onto the valve element so as to surround it when the latter expands to its original condition.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIG. 1 is a transverse cross-sectional view of a needle and hub assembly for use with the medical valve element of the present invention;

FIG. 2 is a transverse cross-sectional view of the medical valve element of the present invention;

FIG. 3 is a plan view of a straight-through-type medical connector embodiment of the present invention utilizing the components of FIGS. 1 and 2;

FIG. 4 is a view, in section, taken along line 1—1 of FIG. 3 with protective caps covering the inlet and outlet of the medical connector and a Luer nut attached;

FIG. 5 is a transverse cross-sectional view of the device of FIG. 4 with the protective caps and Luer nut removed and a female Luer fitting attached to open the valve;

FIG. 6 is a transverse cross sectional view of a Y-site port-type connector embodiment of the present invention utilizing the components of FIGS. 1 and 2;

FIG. 7 is a transverse plan view of a device that fits the collar around the valve element of the invention using the method of the invention.

DESCRIPTION OF THE PREFERRED EMBODIMENTS

FIG. 1 is a cross-sectional view of a cannula 21 for use according to the present invention. The cannula 21 is mounted on a hub 23 which has a body portion 25 formed on the cannula opposite the cannula's point 27. The cannula 21 has a lumen 29 which extends through the cannula from the point 27 to a cannula end 31 opposite the point 27. Point 27 is bent slightly inward towards the longitudinal axis of lumen 29. The hub body portion 25 has a valve element locking recess 32 formed adjacent one end thereof. The other end of the hub body portion 25 is mounted about the cannula end 31 and tapers radially outward therefrom to a shoulder 33, on which a peripheral notch 35 is formed.

Referring now to FIG. 2, there is shown the elongated valve element 37 of the present invention. The valve element 37 is generally cylindrical in exterior configuration over its length. The valve element 37 has a first portion 39 which has generally a solid circular cross-section with a base 41 forming a first end of the valve element 37 and extending to a tip 43. The valve element has a second portion 45 which has a frustoconical interior passage 47 that tapers slightly outwardly from tip 43 to second portion 49. The third portion 51 has an interior cylindrical passage 53 that extends from second portion 49 to base 55. Grooves 57 run about the circumference of interior cylindrical passage 53. Peripheral flange 59 runs around the exterior of valve element 37 and is formed adjacent to base 55. Valve element portions 39, 45 and 51 are axially aligned with one another and provide a central passageway consisting of passageways 47 and 53.

As will be seen in FIG. 2, solid metallic collar 61 is in interference fit with first portion 39 of valve 37 so as to exert a radially compressive force upon first portion 39. Dimensions such as an inner diameter for metallic collar 61 of 0.126 inches and an outer diameter for first portion 39 of 0.145 inches would achieve the desired radially compressive force. These dimensions are presented by way of illustration only and are not intended to constitute limits on the practice of the present invention. The valve element 37 also has a peripheral flap or enlarged annular ring 63 formed on the first portion 39 adjacent the base 41 to help prevent the solid metallic collar 61 from sliding off of valve element 37.

Referring now to FIGS. 3 and 4, there is shown a straight-through-type medical connector 65 embodiment of the present invention. FIG. 3 is a plan view of medical connector 65 with a body 66 having an inlet portion 67, an outlet portion 69 and a main body portion 71. Formed on the external surface thereof are two laterally-opposed gripping surfaces 73, 75 which assist the medical personnel during the use of the device as will be apparent to those skilled in the art. A neck 76 is formed at the intersection of the outlet portion 69 and main body portion 71. As seen in FIG. 4, a longitudinal passage 77 extends through the interior of the inlet portion 67. The inlet portion 67 has an inlet 79, from which the longitudinal passage 77 tapers inward slightly over most of its length, and external threads 81. Contamination cap 83 engages external threads 81 so as to cover inlet 79. The outlet portion has an outlet 85 onto which outlet passage 87 opens. The main body portion 71 has a longitudinal passage 89 extending therethrough and opening into the inlet passage 77 and the outlet passage 87 so that all three passages 77, 87, 89 are axially aligned so as to provide a conduit through the connector 65. Dust cap 91 grips outlet portion 69 so as to cover outlet 85. Swivel Luer nut 93 rotatably engages neck 76 so as to allow connection of surgical tubing to outlet portion 69. Valve 94 of the present invention, consisting of the cannula 21 and hub 23 shown in FIG. 1, disposed within the valve element 37 shown in FIG. 2, is located within the conduit formed by passages 77, 87 and 89.

Disposed at the intersection of outlet passage 87 and longitudinal passage 89 is peripheral ridge 95. Peripheral ridge 95 engages peripheral notch 35 of hub 23 so as to hold hub 23 and cannula 21 of FIG. 1 within longitudinal passage 89. Hub 23 and cannula 21 are disposed within passages 47 and 53 of valve element 37 of FIG. 2. Base 55 of valve element 37, with the aid of flange 59, engages the valve element locking recess 32 of the hub 23. As will be seen in FIG. 4, the valve element first portion 39 at its base 41 is at least even with and should extend slightly beyond the inlet 79 so that the base 41 can be readily swabbed with disinfectant prior to use to insure sterility.

Referring now to FIG. 5, Luer-type fitting 97 is shown engaging threads 81 so as to be attached to medical connector 65. Luer-type fitting 97 has a nose 99 of conventional construction, i.e., slightly tapered, through which a passageway 101 extends in communication with surgical tubing 103. The medical connector 65 has a surgical-type outlet tube 105 extending through the outlet 85 so as to be in communication with outlet passage 87. In the attachment process, the Luer fitting nose 99 presses against the base 41 of the valve element first portion 39 so as to compress the valve element third portion 51 against the hub 23. Grooves 57 allow for easier compression of valve element third portion 51. This compression permits the Luer fitting nose 99 to force the valve element first portion 39 onto the point 27 of the cannula 21 and, after the point 27 pierces the first portion 39, the first portion 39 is forced inwardly along the cannula 21 so as to open a path for fluid communication from the surgical tubing 103 through the passageway 101 formed in the Luer fitting 97 and the cannula lumen 29. Due to the slight bend of point 27, the valve element first portion 39 is pierced near the center of its base 41, along the longitudinal axis of cannula lumen 29. Because the valve element 37 is formed of a flexible and resilient material, removal of the Luer fitting 97 from the medical connector 65 decompresses the valve element third portion 51 so the that valve element first portion 39 moves outwardly away from the hub 23 to its original position as shown in FIG. 4. The first portion 39 is subjected to compressive radial forces exerted by surrounding solid metallic collar 61 so that the movement of the first portion 39 off the cannula 21 and beyond the cannula point 27 then seals, once more, the fluid passageway which existed through the cannula lumen 29 in the utilization shown in FIG. 5.

Referring now to FIG. 6, there is shown an alternate embodiment of a Y-site port type connector 107 according to the present invention. The port 107 has a body 109 from which extends an outlet arm 111, a first inlet arm 113, and a second inlet arm 115. Luer-type threads 117 extend outwardly from the first arm 113 for use in attaching other medical devices to the arm 113. If desired, the threads 117 may be omitted, or similar threads may be added to the other arms 115, 111. As is seen in FIG. 6, the first arm 113 and second arm 115 intersect one another at an acute angle and the arm 113 is generally longitudinally aligned with the outlet arm 111. Any other configuration may be equally used with respect to the present invention.

As is seen in FIG. 6, the outlet arm 111 is hollow and generally circular in cross-section with a outlet passage 119 extending from an outlet 121 formed on the outlet arm 111 inwardly toward the inlet arms 113, 115. The inlet arm 113 has a passage 123 which extends from a first arm inlet 125 toward the outlet arm passage 119. The second inlet arm 115 has a second arm inlet 127, from which a second inlet passage 129 extends toward the outlet passage 119. The outlet passage 119 and inlet passages 123, 129 meet in a central chamber 131. For the particular embodiment shown in FIG. 6, the central chamber 131 is axially aligned with the first inlet arm passage 113 and the outlet arm passage 111. The second inlet arm passage 129 communicates with the central chamber 131 through a chamber extension 133. Obviously, it is not necessary that the outlet arm 111 be aligned with either of the inlet passages 129, 123, so long as the three passages 119, 123 and 129 communicate directly with one another, such as by the central chamber 131 and chamber extension 133 shown in FIG. 6.

The valve 94 is shown in FIG. 6 disposed within the first inlet arm bore 123. The valve 94 is seen to consist of the cannula 21 and hub 23 shown in FIG. 1, disposed within the valve element 37 shown in FIG. 2. Similar to the configuration shown in FIG. 4, peripheral ridge 95 in first inlet arm bore 123 engages peripheral notch 35 of hub 23 so as to hold hub 23 and cannula 21 of FIG. 1 within inlet arm bore 123. Base 55 of valve element 37, with the aid of flange 59, engages the valve element locking recess 32 of the hub 23.

In fitting the solid metallic collar 61 onto valve element 37 during manufacture of the valve element, a device such as the one shown in FIG. 7 may be used. Input air hose 135 provides a source of pressurized sterile gas, such as deionized air, that is delivered upon actuation via a foot operated switch or some similar control mechanism. Input air hose 135 is connected to air blast tube 137 which directs the flow of pressurized air vertically downwards. Upper bracket 139 features upper bushing 140 and is attached to vertical rack 141. Upper bracket 139 and upper bushing 140 support air blast tube 137 in a vertically slidable manner. Air blast tube 137 slides vertically when vertical force is applied to blast tube handle 142.

Valve load barrel 143 is supported in a like manner by lower bracket 145, which is also attached to vertical rack 141, and lower bushing 146. Lower bushing 146, as well as upper bushing 140, may be constructed of resin material such as Teflon® or Delrin®, both manufactured by E. I. DuPont de Nemours & Company of Wilmington, Del. These materials are described by way of example only and are not intended to constitute limitations upon the practice of the present invention. Valve load barrel 143 runs through coil spring 147 along the latter's longitudinal axis. Load barrel collar 148 clamps around valve load barrel 143 so that movement of coil spring 147 is restricted on the upper end by load barrel collar 148 and on the lower end by lower bracket 145. As valve load barrel 143 slides vertically downwards, coil spring 147 is compressed in resistance between load barrel collar 148 and lower bracket 145. The bore through valve load barrel 143 has a diameter at the top slightly larger than that of valve element 37. The bore then tapers down to a diameter at the bottom of valve load barrel 143 of less than solid metallic collar 61.

Ring nest 149 is also attached to vertical rack 141 and contains an upper bore 151 through its top portion. The diameter of upper bore 151 is slightly larger that the outer diameter of the solid metallic collar 61 and has a depth equal to the width of collar 61. A lower bore 153 with a diameter slightly less than the inner diameter of solid metallic collar 61 is located adjacent to and beneath upper bore 151 and has a depth equal to the distance between the base 41 of valve element 37, as shown in FIG. 2, and the edge of the solid metallic ring 61 nearest to the base 41. The upper bore 151 and lower bore 153 are axially aligned with one another.

In operation, valve element 37, prior to the installation of solid metallic collar 61, is placed partially within the top of valve load barrel 143. The taper of valve load barrel 143 holds valve element 37 in its initial position as shown in FIG. 7. Solid metallic collar 61 is placed in upper bore 151 in ring nest 149. Handle 142 is then pulled downwards so that the lower end of air blast tube 137 and upper end of valve load barrel 143 engage so as to seal. As further downward force is applied to handle 142, valve load barrel 143 is pushed downward so that its lower end 154 abuts ring nest 149 so that the bore through valve load barrel 143 and upper bore 151 in ring nest 149 are axially aligned. Air blast tube 137 and valve load barrel 143 are held in this position via constant force applied to handle 142 as a blast of deionized air is then delivered through input air hose 135 and air blast tube 137 upon actuation of the input air control switch. The blast of air propels valve element 37 down through valve load barrel 143.

The taper of the bore of valve load barrel 143 compresses valve element 37 so that it has a diameter smaller than that of solid metallic collar 61 upon exit of the bottom of valve load barrel 143. Upon exit from valve load barrel 143, compressed valve element 37 is directed into bores 151 and 153, and thus through solid metallic collar 61, in ring nest 149. Valve element 37, upon expansion to its original diameter, is then fitted with the solid metallic collar as shown in FIG. 2.

Upon release of force from handle 142, coil spring 147 exerts an upward force on valve load barrel 143 so that it lifts away from ring nest 149. The fitted valve element may then be removed from ring nest 149.

The various components of the medical connectors and ports of the present invention are molded from conventional medical grade plastics. For example, valve element 37 may be molded of medical grade latex, such as 7377-30 gum formulated to 80 Shore A durometer hardness, formulated and molded by West Company of Philadelphia, Pa. The medical connector body 66 or port body 109 may be injection molded from medical grade polypropylene, such as grade PD-626 Pro-fax® polypropylene distributed by Himont U.S.A., Inc. of Wilmington, Del. The cannula 21 and solid metallic collar 61 may be made be made of #304 stainless steel. The needle hub 23 may be injection molded from medical grade polypropylene or from medical grade polycarbonate, such as from Calibre® 200-15 poylcarbonate resin manufactured by Dow Chemical Company of Midland, Mich. The foregoing materials are described by way of example only, and are not intended to constitute limitations upon the practice of the present invention, as defined by the following claims.

It will be apparent to those skilled in the art that the present invention can be embodied in other forms of medical valves and connectors and that modifications and variations therefrom can be made without departing from the spirit and scope of this invention. Accordingly, this invention is to be construed and limited only by the scope of the appended claims.

What is claimed is:

1. An elongated flexible valve element for medical use comprising:

a first portion of solid circular cross-section, said first portion having an outer end which includes an enlarged annular ring formed thereon;

a second portion of generally circular cross-section adjacent to the first portion with a longitudinal central passage therethrough; and, a collar surrounding said first portion of said valve element and exerting a radially compressive force thereon said collar being positioned between said enlarged annular ring and said second portion of said flexible valve element.

2. The medical valve element of claim 1 wherein said collar is a solid ring.

3. The medical valve element of claim 1 wherein said second portion includes a frustoconically shaped interior passage adjacent said first portion and a cylindrical interior passage extending therefrom, said cylindrical interior passage having at least one peripheral groove on the wall surface thereof.

4. A medical valve for use in a medical connector having an inlet port and an outlet port and an inner passage extending through said medical connector from said inlet port to said outlet port to define a conduit inner passage in said medical connector, said medical valve comprising:

a cannula having a piercing tip;

a hub in fixed and surrounding relation to said cannula;

means for fixing said hub within the conduit inner passage with the piercing portion of the cannula directed toward the conduit inlet;

an elongated flexible valve element having a first portion of solid circular cross-section and a second portion of generally circular cross-section adjacent to the first portion with a longitudinal central passage therethrough, said first portion having an outer end which includes an enlarged annular ring formed thereon;

a collar surrounding said first portion of said valve element, said collar being positioned between said enlarged annular ring and said second portion of said flexible valve element and being sized to exert a radially compressive force on said first portion of said valve element; and, means for securing the valve element to the hub.

5. The medical valve as defined in claim 4 wherein said means for fixing said hub within said conduit inner passage includes a hub annular body portion dimensioned to engage a portion of the surface of said conduit inner passage to retain said hub and said cannula within said conduit inner passage.

6. The medical valve as defined in claim 4 wherein said means for securing the valve element to the hub includes a peripheral flange at the end of said second portion of said valve element opposite said first portion of said valve element and an annular ridge in said hub dimensioned so that the peripheral flange is compressed between the hub annular ridge and the surface of said conduit inner passage so as to hold the valve element within said conduit inner passage.

7. A medical connector comprising:
   a connector main body with an outlet and an inlet, and in which the inlet and the outlet each have a passage extending therefrom through the main body so as to be in communication with one another to provide a fluid passageway between the inlet and the outlet;
   a cannula having a piercing tip;
   a hub in fixed and surrounding relation to said cannula;
   means for fixing said hub within said fluid passageway with the piercing portion of said cannula directed towards said inlet;
   an elongated flexible valve element received within the fluid passageway, said valve element including a first portion of solid circular cross-section and a second portion of generally circular cross-section adjacent to the first portion with a longitudinal central passage therethrough said first portion having an outer end which includes an enlarged annular ring formed thereon;
   a collar surrounding said first portion of said valve element, said collar being sized to exert a radially compressive force on said first portion of said valve element, said collar being positioned between said enlarged annular ring and said second portion of said flexible valve element; and,
   means for securing the valve element to the hub.

8. The medical connector as defined in claim 7 wherein said means for fixing said hub within said connector fluid passageway includes a hub annular body portion dimensioned to engage a portion of the surface of said connector fluid passageway to retain said hub and said cannula within said connector fluid passageway.

9. The medical connector as defined in claim 7 wherein said means for securing the valve element to the hub includes a peripheral flange at the end of said second portion of said valve element opposite said first portion of said valve element and an annular ridge in said hub dimensioned so that the peripheral flange is compressed between the hub annular ridge and the surface of said connector fluid passageway so as to hold the valve element within said connector fluid passageway.

10. The medical connector as defined in claim 7 wherein said inlet of said connector main body is configured to be received within a female Luer type connector.

11. A Y-site port medical connector comprising:
   a connector body having an axial passageway therein and a first inlet port and an outlet port in flow communication with said axial passageway, an inlet arm having a second passageway, said second passageway having a second inlet port and an internal outlet in flow communication with the outlet port of said connector body;
   a cannula having a piercing tip;
   a hub in fixed and surrounding relation to said cannula;
   means for fixing said hub within said axial passageway with the piercing portion of said cannula directed towards said first inlet port;
   an elongated flexible valve element received within the axial passageway, said valve element including a first portion of solid circular cross-section and a second portion of generally circular cross-section adjacent to the first portion with a longitudinal central passage therethrough said first portion having an outer end which includes an enlarged annular ring formed thereon;
   a collar surrounding said first portion of said valve element said collar being sized to exert a radially compressive force on said first portion of said valve element, said collar being positioned between said enlarged annular ring and said second portion of said flexible valve element; and,
   means for securing the valve element to the hub.

12. The Y-site port medical connector as defined in claim 11 wherein said means for fixing said hub within said axial passageway includes a hub annular body portion dimensioned to engage a portion of the surface of said axial passageway to retain said hub and said cannula within said axial passageway.

13. The Y-site port medical connector as defined in claim 11 wherein said means for securing the valve element to the hub includes a peripheral flange at the end of said second portion of said valve element opposite said first portion of said valve element and an annular ridge in said hub dimensioned so that the peripheral flange is compressed between the hub annular ridge and the surface of said axial passageway so as to hold the valve element within said axial passageway.

14. The medical connector as defined in claim 11 wherein said first inlet port of said connector body is configured to be received within a female Luer type connector.

15. The medical connector as defined in claim 11 wherein said second inlet port of said connector body is configured to be received within a female Luer type connector.

16. A medical valve comprising:
   a conduit having an inflow port and an outflow port, an inner passage extending through said conduit interconnecting said inflow and outflow ports, said inflow port configured to be coupled to a Luer type connector;
   a hub member retained within said conduit and including an upstream end and a downstream end;
   a cannula extending from said hub member and having a first cannula end disposed near said inflow port and a second cannula end extending axially away from said first cannula end, said cannula including an inner lumen for establishing a fluid flow passage between said first and second cannula ends;
   a resilient valve element having a generally cylindrical first end portion configured to fit within said conduit inflow port, said first end portion of said resilient valve element having an outer end which includes an enlarged annular ring formed thereon and being axially movable from a first location within said inner passage of said conduit to a second location within said inner passage of said conduit for piercing penetration by said first end of said cannula when said inflow port of said conduit is coupled to a mating Luer fitting to thereby form a passage in said first end portion of said resilient valve element, said resilient valve element being axially movable from said second location toward said first location when the inflow port of said conduit is disconnected from said mating Luer fitting to effect withdrawal of said cannula first end and thereby substantially close said passage in said first end portion of said resilient valve element;

a collar on the cylindrical surface of said first end portion of said resilient valve element, said collar being positioned between said enlarged annular ring and said second portion of said resilient valve element, said collar having an inner diameter sized to exert a radially compressive force thereon which is sufficient to effect a closing of the passage therein to prevent fluid flow therethrough.

17. The medical valve of claim 16 wherein said collar is formed of metal.

18. The medical valve of claim 16 wherein said collar is formed of stainless steel.

* * * * *